US006569902B2

(12) United States Patent
Floyd et al.

(10) Patent No.: US 6,569,902 B2
(45) Date of Patent: May 27, 2003

(54) NITRONE INHIBITION OF CANCER DEVELOPMENT

(75) Inventors: Robert A. Floyd, Oklahoma City, OK (US); Yashige Kotake, Oklahoma City, OK (US); Kenneth L. Hensley, Oklahoma City, OK (US); Dai Nakae, Nara (JP)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/819,570

(22) Filed: Mar. 28, 2001

(65) Prior Publication Data

US 2002/0004531 A1 Jan. 10, 2002

Related U.S. Application Data

(60) Provisional application No. 60/193,572, filed on Mar. 30, 2000.

(51) Int. Cl.$^7$ .......................... A01N 33/02; A01N 33/24; A61K 31/13; A61K 31/15; C07C 291/04

(52) U.S. Cl. ........................ 514/638; 514/640; 514/645; 564/248; 564/300

(58) Field of Search ................................ 514/638, 640, 514/645; 564/248, 300

(56) References Cited

PUBLICATIONS

Database CAPLUS on STN, Acc. No. 1991:663464, Carney et al., 'Pharmaceutical compositions containing free radical scavengers for the treatment of oxidative cell damage.' WO 9105552 (abstract).*
Database CAPLUS on STN, Acc. No. 1996:658269, Yamashita et al., 'The effects of alpha phenyl tert–butyl nitrone (PBN) on copper–induced rat fulminate hepatitis with jaundice.' Free Radical Biol. Med. (1996), 21(6), pp. 755–761 (abstract).*
Cao et al., "α–Phenyl–tert–butyl–nitrone Reduces Cortical Infarct and Edema in Rats Subjected to Focal Ischemia," *Brain Res.*, 644:267–272, 1994.
Carney et al., "Reversal of Age–related Increase in Brain protein Oxidation, Decrease in Enzyme Activity, and Loss in Termporal and Spacial Memory by Chronic Administration of the Spin–trapping Compound N–tert–butyl–α–phenyl–nitrone," *Proc. Natl. Acad. Sci. USA*, 88:3633–3636, 1991.
Cerda et al., "Influence of oxygen Ratical Injury on DNA Methylation," *Mutat. Res.*, 386:141–152, 1997.
Chemoprevention Working Group. (1999) *Cancer Res.* 59, 4743–4358.
Christman J.K., "Lipotrope Deficiency and Persistent Changes In DNA Methylation: Lipotrope Deficiency and DNA Methylation," *Adv. Exp. Med. Biol.*, 375:97–106, 1995.

Clough–Helfman et al., "The Free Radical Trapping Agent N–tert–butyl α–phenylnitrone (PBN) Attenuates Cerebral Ischaemic Injury in Gerbils," *Free Radic. Res. Commun.*, 15:177–186, 1991.
Endoh et al., Inhibition by Acetylsalicylic Acid, a Cyclo–Oxygenase Inhibitor, and p–bromophnacylbromide, a Phosphoipase $A_2$ Inhibitor, of Both Cirrhosis and Enzyme–Altered Nodules Caused by a Choline–Deficient, L–amino Acid–Defined Diet in Rats, "*Carcinogenesis*", 17:467–475, 1996.
Fallon, J., Matthews, R. T., Hyman, B. T. & Beal, M. F. (1997) *Exp. Neurol.* 144, 193–198.
Farber, E. (1996) *Adv. Cancer Res.* 70, 21–48.
Nakae, D., Mizumoto, Y., Yoshiji, H., Andoh, N., Horiguchi, K., Shiraiwa, K., Kobayashi, E., Endoh, T., Shiimoji, N., Tamura, K., Tsujiuchi, T., Denda, A. & Konishi, Y. (1994) *Jpn. J. Cancer Res.* 85, 499–505.
Nakae D., "Endogenous Liver Carcinogenesis in the Rat," *Pathol. Int.*, 49:1028–1942, 1999.
Nakae D., "Modulation by Environmental Chemicals of Liver Carcinogenesis in Rats", *Recent Res. Devel. Cancer*, 2:143–165, 2000.
Nose, K. (2000) *Biol. Pharm. Bull.* 23, 897–903.
Novelli et al., "Anti–shock Action of Phenyl–tert–butyl–nitrone, a Spin Trapper," *In: Oxygen Free Radicals in Shock*, edited by G.P. Novelli and F. Ursini, Florence: Karger, Basel, 1986, pp. 119–124.
Ohata et al., "Inhibition by 1'–acetoxychavicol Acetate of Lipopolyvsaccharide– and Interferon–γ–induced Nitric Oxide production Through Suppression of Inducible Nitric Oxide Synthase Gene Expression in RAW263 Cells," *Carcinogenesis*, (Lond.), 19:1007–1012, 1998.
Pahlmark et al., "Effects of the Spin Trap–α–phenyl–N–tert–butyl nitrone (PBN) in Transient Forebrain Ischaemia in the Rat," *Acta Physiol. Scand.*, 157:41–51, 1996.

(List continued on next page.)

*Primary Examiner*—Brian Davis
(74) *Attorney, Agent, or Firm*—Fulbright & Jaworski

(57) ABSTRACT

PBN (α-phenyl-tert-butylnitrone), and its derivatives nitrone-based free radical traps, significantly reduce preneoplastic nodule development as well as inhibit hepatocellular carcinoma (HCC) formation at very low levels. The involvement of reactive oxygen species (ROS) in cancer development has been strongly implicated for many years. The involvement of ROS has been strongly implicated in cancer development is a model system where feeding a choline deficiency (CD) diet to rats leads to hepatocellular carcinoma (HCC) development. Administering PBN in the drinking water inhibits HCC formation. Preoplastic nodule growth in the liver is significantly suppressed by administering PBN, or some of its natural metabolites, in the diet. The effectiveness of PBN in preventing HCC development in the CD liver model is considered due to its prevention of tumor development after the target cells have already been initiated, i.e. genetically changed into tumor cells. Administration of PBN (or its potent derivatives) to humans that may already have microscopic tumor preneoplastic nodules should prevent the eventual frank tumor formation.

13 Claims, 4 Drawing Sheets

OTHER PUBLICATIONS

Pitot, H. C., Campbell, H. A., Matonpot, R., Bawa, N., Rizvi, T. A., Xu, Y. H., Sargent, L., Dragan, Y. & Pyron, M. (1989) *Toxicol. Pathol.* 17, 594–612.

Pogrebniak, H., Matthews, W., Mitchell, J., Russo, A., Samuni, A. & Pass, H. (1991) *J. Surg. Res.* 50, 469–474.

Pogrebniak et al., "Spin Trap Salvage From Endotoxemia: The Role of Cytokine Down–Regulation," *Surgery*, 112:130–139, 1992.

Poirier L.A., "Methyl Group Deficiency in Hepatocarcinogenesis," *Drug Metab. Rev.*, 26: 185–199, 1994.

Poyer et al., "Spin Trapping of the Trichloromethyl Radical Produced During Enzymic NADPH Oxidation in the Presence of Carbon Tetrachloride or Carbon Bromotrichloromethane," *Biochim. Biophys. Acta*, 539:402–409, 1978.

Reed, J.C. (1999) *J. Clin. Oncol.* 17, 2941–2953.

Reinke, L. A., Moore, D. R., Sang, H., Janzen, E. G. & Kotake, Y. (2000) *Free Radic. Res. Biol. Med.* 28, 345–350.

Robinson, K. A., Stewart, C. A., Pye, Q. N., Nguyen, X., Kenney, L., Salzman, S., Floyd, R. A. & Hensley, K. (1999) *J. Neurosci. Res.* 55, 724–732.

Sakata et al., "the Prolyl 4–hydroxylase Inhibitor HOE077 Prevents Activation of Ito Cells, Reducing procollagen Gene Expression In Rat Liver Fibrosis Induced by Choline–Deficient L–amino Acid–defined Diet," *Hepatology*, 23:755–763, 1996.

Sang, H., Wallis, G. L., Stewart, C. A. & Kotake, Y. (1999) *Arch. Biochem. Biophys.* 363, 341–348.

Sasaki et al., "Alterations of the Transforming Growth Factor–β Signaling Pathway in Hepatocellular Carcinomas Induced Endogenously and Exogenously in Rats," *Jpn. J. Cancer Res.*, 92:16–22, 2001.

Schulz, J. B., Henshaw, D. R., Siwek, D., Jenkins, B. G., Ferrante, R. J., Cipolloni, P. B., Kowall, N. W., Rosen, B. R. & Beal, M. F. (1995) *J. Neurochem.* 64, 2239–2247.

Stewart, C. A., Hyam, K., Wallis, G., Sang, H., Robinson, K. A., Floyd, R. A., Kotake, Y. & Hensley, K. (1999) *Arch. Biochem. Biophys.* 365, 71–74.

Tabatabaie et al., In Vivo Trapping of Nitric Oxide in the Brain of Neonatal Rats Treated with the HIV–1 Envelope Protein gp 120: Protective Effects of α–Phenyl–tert–butylnitrone. *Biochem. Biophys. Res. Commun.*, 221:386–39–. 1996.

Tsutsumi, Y., Serizawa, A. & Kawai, K. (1995) *Pathol. Int.* 45, 108–115.

Tsujiuchi, T., Kobayashi, E., Nakae, D., Mizumoto, Y., Andoh, N., Kitada, H., Ohashi, K., Fukuda, T., Kido, A., Tsutsumi, M., Denda, A. & Konishi Y. (1995) *Jpn. J. Cancer Res.* 86, 1136–1142.

Wyllie, A. H., Bellamy, C. O., Bubb, V. J., Clarke, A. R., Corbet, S., Curtis, L., Harrison, D. J., Hooper, M. L., Toft, N., Webb, S. & Bird, C. C. (1999) *Br. J. Cancer* 80, Suppl. 1, 34–37.

Yoshiji, H., Nakae, D., Mizumoto, Y., Horiguchi, K., Tamura, K., Denda, A., Tsujii, T. & Konishi, Y. (1992) *Carcinogenesis* 13, 1227–1233.

Zeisel S.H., "Nutrients, Signal Transduction and Carcinogenesis," *Adv. Exp. Med. Biol.*, 369:175–183, 1995.

Floyd et al., "Spin Trapping in biological Systems. Oxidation of the Spin Trap–5,5–dimethyl–1–pyrroline–1–oxide by a Hydroperoxide–hematin System," *Biochem. Biophys. Res. Commun.*, 74:79–84, 1977.

Floyd et al., "Role of Oxygen Free Radicals in Carcinogenesis and Brain Ischemia," *FASEB J.*, 4:2587–2597, 1990.

Floyd et al., "Nitrone Radical Traps Protect in Experimental Neurodegenerative Diseases," In: *Neuroprotective Approaches to the Treatment of Parkinson's Disease and other Neurodegenerative Disorders*, edited by C.A. Chapman, C.W. Olanow, P. Jenner, and M. Youssim, London: Academic Press Limited, 1996, pp. 69–90.

Floyd, R.A., "Protective Action of Nitrone–Based Free Radical Traps Against Oxidative Damage to the Central Nervous System," *Adv. Pharmacol.*, 38:361–378, 1997.

Floyd et al., "Inhibition by Phenyl N–tert–butyl Nitrone of Early Phase Carcinogenesis in the Livers of Rats Fed a Choline–Deficient, L–amino Acid–defined Diet," *Cancer Res.*, 58:4548–4551, 1998.

Folbergrova et al., N–tert–butyl–α–phenylnitrone Improves Recovery of Brain Energy State in Rats following Transient Focal Ischemia, *Proc. Natl. Acad. Sci. USA*, 92:5057–5061, 1995.

Gold, R., Schmied, M., Giegerich, G., Breitschopf, H., Hartung, H. P., Toyaka, K. V. & Lassmann, H. (1994) *Lab. Invest.* 71, 219–225.

Goshal et al., "Prevention by Free Radial Scavenger $AD_5$ of Prooxidant Effects of Choline Deficiency," *Free Radic. Biol. Med.*, 8:3–7, 1990.

Harkins, J. D., Carney, J. M., Meier, M., Leak, S. C. & Tobin, T. (1997) *Vet. Hum. Toxicol.* 39, 268–271.

Hautekeete et al., "The Hepatic Stellate (Ito) Cells: Its role in Human Liver Disease," *Virchows Arch.*, 430:195–207, 1997.

Hensley et al., "Nitrone–based Free Radical Traps as Neuroprotective Agents in Cerebral Ischemia and Other Pathologies," In: *Neuroprotective Agents and Cerebral Ischaemia*, edited by A. R. Green and A. J. Cross, London: Academic press Ltd., 1996, p. 229–317.

Hensley et al., "Quantitation of Protein–bound 3–nitrotyrosine and 3,4–dihydroxyphenylalanine by High Performance Liquid Chromatography with Electrochemical Array Detection," *Anal. Biochem.*, 251:187–195, 1997.

Hensley et al., "Interaction of α–phenyl–N–tert–butyl Nitrone and Alternative Electron Acceptors With Complex I Indicates a Substrate Reduction Site Upstream from the Rotenone Binding Site," *J. Neurochem*, 71:2549–2557, 1998.

Hensley, K., Kotake, Y., Sang, H., Pye, Q. N., Kolker, W. G. L., Tabatabaie, T., Stewart, C. A., Konishi, Y., Nakae, D. & Floyd, R. A. (2000) *Carcinogenesis* 21, 983–989.

Hursting, S. D., Slaga, T. J., Fischer, S. M., DiGiovanni, J. D. & Phang, J. M. (1999) *J. Natl. Cancer Inst.*. 91, 215–225.

Janzen, E.G., "Spin Trapping," *Acc. Chem. Res.*, 4:31–40, 1971.

Janzen, E. G. & Haire, D. L. (1990) in *Advances in Free Radical Chemistry*, ed. Tanner D. D. (JAI Press, Greenwich), pp. 253–295.

Janzen et al., "Comparison of Antioxidant Activity of PBN with Hindered Phenols in Initiated Rat Liver Microsomal Lipid Peroxidation," In: *Frontiers of Reactive Oxygen Species in Biology and Medicine*, edited by K. Asada and T. Toshikawa, Elsevier Science, 1994, pp. 431–446.

Kishida, H., Nakae, D., Kobayashi, Y., Kusuoka, O., Kitayama, W., Denda, A., Fukui, H. & Konishi, Y. (2000) *Exp. Toxicol. Pathol.* 52, 405–412.

Kobayashi et al., "Prevention by 1'–acetoxychavicol Acetate of the Induction But Not Growth of Putative Preneoplastic, glutathioneS–transferase Placental form–positive, Folcal Lesions in the Livers of Rats Fed a choline–deficient, L–amino Acid–defined Diet"; *Carcinogenesis*, 19(10):1809–1814, 1998.

Kotake, Y. (1999) *Antiox. Redox Signal.* 1, 481–499.

Kotake, Y., Sang, H., Miyajima, T. & Wallis, G. L. (1998) *Biochim. Biophys. Acta* 1448, 77–84.

Krupp, G., Klapper, W. & Parwaresch, R. (2000) *Cell Mol. Life Sci.* 57, 464–486.

Lowe, S. W. & Lin, A. W. (2000) *Carcinogenesis* 21, 485–495.

Maronpot et al., "National Toxicology Program Nomenclature for Hepatoproliferative Lesions for Rats," *Toxicol. Pathol.*, 14:263–273, 1986.

Miyajima et al., "Spin Trapping Agent, phenyl–N–tert–butyl Nitrone, Inhibits Induction of Nitric Oxide Synthase in Edotoxin–induced Shock in Mice," *Biochem. Biophys. Res. Commun.*, 215:114–121, 1995.

Mizumoto, Y., Nakae, D., Yoshiji, H., Andoh, N., Horiguchi, K., Endoh, T., Kobayashi, E., Tsujiuchi, T., Shimoji, N., Denda, A., Tsujii, T., Nagao, M., Wakabayashi, K. & Konishi, Y. (1994) *Carcinogenesis* 15, 241–246.

Mori, H., Sugie, S., Yoshimi, N., Hara, Y. & Tanaka, T. (1999) *Mutat. Res.* 428, 291–298.

Nakae, D., Kotake, Y., Kishida, H., Hensley, K. L., Denda A., Kitayama, W., Tsujiuchi, T., Sang, H., Stewart, C.A., Tabatabaie, T., Floyd, R. A. & Konishi, Y. (1998) *Cancer Res.* 58, 4548–4551.

Nakae, D., Yoshiji, H., Mizumoto, Y., Horiguchi, K., Shiraiwa, K., Tamura, K., Denda, A. & Konishi, Y. (1992) *Cancer Res.* 52, 5042–5045.

Nakae, D., Yoshiji, H., Maruyama, H., Kinugasa, T., Denda, A. & Konishi, Y. (1990) *Jpn. J. Cancer Res.* 81, 1081–1084.

Nakae, D., Mizumoto, Y., Kobayashi, E., Noguchi, O & Konishi, Y. (1995) *Cancer Lett.* 97, 233–239.

Nakae, D., Yamamoto, K., Hoshiji, H., Kinugasa, T., Maruyama, H., Farber, J. L. & Konishi, Y. (1990) *Am. J. Pathol.* 136, 787–795.

* cited by examiner

FIG. 1

*Effects of PBN on the induction of HCA, HCC and fibrosis in rats fed the CDAA diet for 70 weeks*

| Group | Treatments (First 26 weeks) | Treatments (Last 44 weeks) | Initial number of rats | Effective number of rats | Final body weight (g) | Reltive liver weight (g/100 g body weight) | Induction of neoplastic lesions HCA — Number of baring rats | HCA Incidence (%) | HCC Number of baring rats | HCC Incidence (%) | Grade of fibrosis (Percent area occupied by collagen fiber in the specimen) |
|---|---|---|---|---|---|---|---|---|---|---|---|
| 1 | CDAA | CDAA | 10 | 7 | $415 \pm 27^a$ | $4.45 \pm 0.26^a$ | 4 | 57.1 | 4 | 57.1 | $13.32 \pm 1.57^a$ |
| 2 | CDAA + PBN | CDAA + PBN | 10 | 8 | $408 \pm 34$ | $4.52 \pm 0.07$ | 2 | $25.0^b$ | 2 | $25.0^b$ | $9.95 \pm 1.17^b$ |
| 3 | CDAA + PBN | CDAA | 10 | 7 | $406 \pm 58$ | $4.40 \pm 0.24$ | 2 | $28.6^b$ | 0 | $0^b$ | $8.71 \pm 1.12^b$ |
| 4 | CDAA | CDAA + PBN | 10 | 8 | $399 \pm 39$ | $4.23 \pm 0.63$ | 5 | 62.5 | 0 | $0^b$ | $12.86 \pm 1.65$ |
| 5 | CSAA | CSAA | 10 | 10 | $475 \pm 31^b$ | $2.90 \pm 0.10^b$ | 0 | $0^b$ | 0 | $0^b$ | $1.61 \pm 0.22^b$ |
| 6 | CSAA + PBN | CSAA + PBN | 10 | 10 | $446 \pm 15$ | $3.26 \pm 0.26$ | 0 | 0 | 0 | 0 | $1.58 \pm 0.13$ |

[a] Values are presented as means ± standard deviations.
[b] Significantly different from the group 1 value.

FIG. 2

| Group | Treatment(s) | Effective number of rats | Final body weight (g) | Relative liver weight (g/100 g body weight) | Average food intake (g/kg body weight /day) | Average exposure to PBN derivatives (mg/kg body weight /day) |
|---|---|---|---|---|---|---|
| 1 | CDAA | 5 | 530 ± 52* | 3.81 ± 0.41 | 63 ± 2 | 0 |
| 2 | CDAA + PBN, low | 5 | 506 ± 61 | 3.47 ± 0.29 | 64 ± 3 | 5.74 ± 0.27 |
| 3 | CDAA + PBN, middle | 5 | 511 ± 24 | 4.17 ± 0.47 | 62 ± 2 | 27.90 ± 1.03 |
| 4 | CDAA + PBN, high | 5 | 506 ± 45 | 3.99 ± 0.54 | 62 ± 2 | 56.08 ± 2.09 |
| 5 | CDAA + 4-OHPBN, low | 5 | 497 ± 45 | 4.10 ± 0.47 | 64 ± 3 | 5.76 ± 0.31 |
| 6 | CDAA + 4-OHPBN, middle | 5 | 505 ± 24 | 4.05 ± 0.56 | 62 ± 2 | 27.74 ± 0.75 |
| 7 | CDAA + 4-OHPBN, high | 5 | 509 ± 11 | 3.91 ± 0.52 | 65 ± 2 | 58.50 ± 1.89 |
| 8 | CDAA + 3-OHPBN, low | 5 | 517 ± 34 | 4.55 ± 0.59 | 64 ± 1 | 5.76 ± 0.13 |
| 9 | CDAA + 3-OHPBN, middle | 5 | 504 ± 29 | 3.89 ± 0.49 | 63 ± 4 | 28.33 ± 1.74 |
| 10 | CDAA + 3-OHPBN, high | 5 | 520 ± 13 | 3.61 ± 0.67 | 63 ± 2 | 56.49 ± 1.67 |
| 11 | CDAA + 2-OHPBN, low | 5 | 564 ± 57 | 3.53 ± 0.35 | 62 ± 3 | 5.62 ± 0.28 |
| 12 | CDAA + 2-OHPBN, middle | 5 | 527 ± 38 | 3.97 ± 0.32 | 64 ± 4 | 28.87 ± 1.73 |
| 13 | CDAA + 2-OHPBN, high | 5 | 524 ± 70 | 4.12 ± 0.43 | 62 ± 3 | 56.06 ± 2.30 |
| 14 | CDAA + 2-SPBN, low | 5 | 522 ± 23 | 3.55 ± 0.78 | 61 ± 2 | 5.49 ± 0.17 |
| 15 | CDAA + 2-SPBN, middle | 5 | 533 ± 10 | 4.00 ± 0.38 | 61 ± 1 | 27.59 ± 0.47 |
| 16 | CDAA + 2-SPBN, high | 5 | 513 ± 40 | 3.92 ± 0.46 | 63 ± 2 | 56.43 ± 1.82 |
| 17 | CSAA | 5 | 499 ± 59 | 2.67 ± 0.46† | 60 ± 2 | 0 |
| 18 | CSAA + PBN, high | 5 | 511 ± 36 | 3.05 ± 0.28 | 61 ± 3 | 57.61 ± 1.30 |
| 19 | CSAA + 4-OHPBN, high | 5 | 512 ± 33 | 2.56 ± 0.19 | 62 ± 1 | 56.42 ± 2.48 |
| 20 | CSAA + 3-OHPBN, high | 5 | 502 ± 25 | 2.59 ± 0.27 | 60 ± 2 | 57.75 ± 3.46 |
| 21 | CSAA + 2-OHPBN, high | 5 | 488 ± 41 | 2.64 ± 0.31 | 63 ± 1 | 56.22 ± 2.82 |
| 22 | CSAA + 2-SPBN, high | 5 | 491 ± 36 | 2.68 ± 0.39 | 61 ± 3 | 56.66 ± 3.49 |

*The values are the means ± standard deviations.
† Significantly different from the group 1 value.

FIG. 3

Numbers and sizes of GST-P-positive liver lesions and levels of oxidative hepatocyte injuries

| Group | Treatment(s) | Effective number of rats | GST-P-positive lesions Numbers (/cm³) | GST-P-positive lesions Sizes (mm³) | 8-OHdG levels (/$10^6$ dGs) | TBARS levels (pmol MDA eq. / mg protein) |
|---|---|---|---|---|---|---|
| 1 | CDAA | 5 | 11.54 ± 9.25* | 0.140 ± 0.111 | 16.76 ± 5.51 | 448 ± 139 |
| 2 | CDAA + PBN, low | 5 | 6.45 ± 2.79 | 0.057 ± 0.036 | 2.94 ± 0.58† | 442 ± 54 |
| 3 | CDAA + PBN, middle | 5 | 6.20 ± 2.11 | 0.106 ± 0.064 | 2.59 ± 0.30† | 429 ± 68 |
| 4 | CDAA + PBN, high | 5 | 6.04 ± 2.63† | 0.027 ± 0.021† | 3.38 ± 0.61† | 235 ± 132† |
| 5 | CDAA + 4-OHPBN, low | 5 | 13.58 ± 5.19 | 0.033 ± 0.034† | 3.79 ± 1.59† | 222 ± 101† |
| 6 | CDAA + 4-OHPBN, middle | 5 | 11.98 ± 0.99 | 0.027 ± 0.011† | 4.94 ± 2.03† | 217 ± 81† |
| 7 | CDAA + 4-OHPBN, high | 5 | 9.91 ± 7.57 | 0.025 ± 0.010† | 2.73 ± 1.16† | 204 ± 66† |
| 8 | CDAA + 3-OHPBN, low | 5 | 8.90 ± 4.01 | 0.165 ± 0.176 | 3.60 ± 1.20† | 411 ± 73 |
| 9 | CDAA + 3-OHPBN, middle | 5 | 7.84 ± 2.81 | 0.067 ± 0.036 | 3.18 ± 0.36† | 457 ± 88 |
| 10 | CDAA + 3-OHPBN, high | 5 | 9.39 ± 4.60 | 0.013 ± 0.007† | 3.18 ± 0.36† | 281 ± 55† |
| 11 | CDAA + 2-OHPBN, low | 5 | 8.62 ± 3.76 | 0.068 ± 0.036 | 14.80 ± 3.74 | 448 ± 139 |
| 12 | CDAA + 2-OHPBN, middle | 5 | 11.52 ± 3.63 | 0.144 ± 0.147 | 18.94 ± 5.10 | 448 ± 139 |
| 13 | CDAA + 2-OHPBN, high | 5 | 7.62 ± 2.95 | 0.034 ± 0.013 | 14.46 ± 2.80 | 445 ± 82 |
| 14 | CDAA + 2-SPBN, low | 5 | 11.46 ± 5.72 | 0.064 ± 0.094 | 16.78 ± 3.61 | 448 ± 139 |
| 15 | CDAA + 2-SPBN, middle | 5 | 9.38 ± 1.61 | 0.187 ± 0.131 | 16.50 ± 6.01 | 448 ± 139 |
| 16 | CDAA + 2-SPBN, high | 5 | 7.62 ± 2.88 | 0.061 ± 0.071 | 16.26 ± 6.55 | 424 ± 117 |
| 17 | CSAA | 5 | 0 † | - | 3.85 ± 1.52† | 13 ± 11† |
| 18 | CSAA + PBN, high | 5 | 0 | - | 5.12 ± 0.81 | 14 ± 12 |
| 19 | CSAA + 4-OHPBN, high | 5 | 0 | - | 3.32 ± 1.07 | 16 ± 10 |
| 20 | CSAA + 3-OHPBN, high | 5 | 0 | - | 2.55 ± 1.59 | 12 ± 10 |
| 21 | CSAA + 2-OHPBN, high | 5 | 0 | - | 3.44 ± 0.53 | 12 ± 8 |
| 22 | CSAA + 2-SPBN, high | 5 | 0 | - | 2.27 ± 1.25 | 14 ± 9 |

*The values are the means ± standard deviations.
†Significantly different from the group 1 value.

FIG. 4

Apoptotic indices, proliferating indices and grade of fibrosis in the livers

| Group | Treatment(s) | Effective number of rats | Apoptotic indices (%) | | Proliferating indices | | Grades of fibrosis (% area occupied by collagen fiber) |
|---|---|---|---|---|---|---|---|
| | | | In the lesions | In the surroundings | In the lesions | In the surroundings | |
| 1 | CDAA | 5 | 3.37 ± 0.83*[†] | 6.70 ± 0.43 | 6.36 ± 0.59[†] | 3.02 ± 0.29 | 0.788 ± 0.290 |
| 4 | CDAA + PBN, high | 5 | 12.75 ± 1.31[†][‡] | 2.39 ± 0.24[‡] | 6.18 ± 0.35[†] | 2.70 ± 0.50 | 0.402 ± 0.019[‡] |
| 7 | CDAA + 4-OHPBN, high | 5 | 9.07 ± 1.03[†][‡] | 2.65 ± 0.65[‡] | 1.99 ± 0.28[†][‡] | 1.49 ± 0.19[‡] | 0.485 ± 0.078[‡] |
| 10 | CDAA + 3-OHPBN, high | 5 | 10.98 ± 1.28[†][‡] | 2.52 ± 0.53[‡] | 5.88 ± 0.34[†] | 3.01 ± 0.40 | 0.458 ± 0.112[‡] |
| 13 | CDAA + 2-OHPBN, high | 5 | 3.48 ± 0.51[†] | 6.12 ± 0.58 | 6.78 ± 0.30[†] | 2.94 ± 0.49 | 0.622 ± 0.257 |
| 16 | CDAA + 2-SPBN, high | 5 | 2.75 ± 0.41[†] | 6.36 ± 0.33 | 6.20 ± 0.14[†] | 2.67 ± 0.33 | 0.551 ± 0.156 |
| 17 | CSAA | 5 | - | 0.22 ± 0.02[‡] | - | 0.52 ± 0.16[‡] | 0.347 ± 0.076[‡] |

*The values are the means ± standard deviations.
[†]Significantly different from the value in the surroundings.
[‡]Significantly different from the group 1 value.

NITRONE INHIBITION OF CANCER DEVELOPMENT

CROSS-REFERENCE TO RELATED APPLICATIONS

Priority is claimed from provisional application U.S. Ser. No. 60/193,572 filed on Mar. 30, 2000, and incorporated by reference herein.

STATEMENT REGARDING FEDERALLY SPONSORED RESEARCH OR DEVELOPMENT

The federal government has rights in the present invention insofar as it was supported in part by the National Institutes of Health Grants NS35747, PO1-AG05119, 5P50-AG05144 and R01 CA82506.

BACKGROUND

Chronic feeding of a choline-deficient-L-amino acid-defined (CDAA) diet containing no carcinogens exerts a strong hepatocarcinogenicity in rats through the development of apparently preneoplastic, focal lesions in the background presence of repeating hepatocyte death and regeneration as well as fibrosis. Oxidative stress appears to play major roles in its underlying mechanisms in association with alteration on the status of various signaling molecules. Phenyl N-tert-butyl nitrone (PBN), a radical trapper, has been shown to inhibit the development of preneoplastic lesions in the early phase of this dietary hepatocarcinogenesis by apparently inhibiting oxidative stress, inducible cyclo-oxygenase activity and fibrogenesis (Floyd et al., 1998).

Reactive oxygen species (ROS) have been implicated in cancer development for many years. A prime example where ROS are strongly implicated is the model system where feeding a choline deficiency (CD) diet to rats leads to hepatocellular carcinoma (HCC) development, i.e. in the complete absence of exposure to any exogenous known carcinogen. Utilizing this model, the present invention concerns novel observations that make it possible to link ROS with key signal transduction pathways that have been shown to be fundamental in cancer initiation and development. The present inventors have shown that mitochondria from CD-livers are changed such that they mediate a significantly higher yield of $H_2O_2$ production. Additionally, for the first time the present inventors have shown that PBN ($\alpha$-phenyl-tert-butyl nitrone) and its derivatives are nitrone-based free radical traps and, significantly reduce preneoplastic nodule development as well as inhibit hepatocellular carcinoma (HCC) formation at very low levels of the compound. PBN and the like are the most potent anti-carcinogens ever studied in this model. To understand these observations the inventors postulate that the CD-regimen mediates changes in mitochondrial membranes such that they produce enhanced levels of $H_2O_2$ and that PBN and the like significantly inhibit the excess $H_2O_2$ production by acting at Complex I. The present inventors further postulate that excess $H_2O_2$ causes an enhanced inactivation of the PTEN tumor suppressor protein, which causes a loss of its phosphatase activity and thereby mediates a shift toward the activation of the AKT-kinase pathway resulting in a decrease in apoptosis-mediated processes but an increase in oncogenic events. The inventors also propose that the cells in preneoplastic nodules which develop in CD-livers are predisposed toward onto-genesis (as opposed to apoptosis) because of the action of excess $H_2O_2$ and certain growth factors (most likely $TGF\beta_1$) and that PBN and the like alter these processes through both inhibition of excess $H_2O_2$ production and also by suppression of enhanced signal transduction processes. The inventors believe that PBN and the like act to cause preneoplastic nodule cells to become predisposed toward apoptic processes leading to inhibition of tumor development.

Studies on the Pharmacological Action of PBN

The compound PBN was first synthesized in the 1950's, but in 1968 it was discovered to be very useful to trap and stabilize free radicals in chemical reactions and hence it was termed a spin-trap (Janzen 1971). Although PBN is the prototype spin-trap several other nitrones have been synthesized and found useful to trap and characterize free radicals in chemical reactions. These spin traps were used in chemical reactions first, but in the mid-1970's they began to be used to trap free radicals in biochemical and biological systems (Floyd et al. 1978; and Poyer et al. 1978, for example). Pharmacokinetic studies have shown that PBN is readily and rapidly distributed almost equally to all tissues, has a half-life in rats of about 132 minutes and is eliminated mostly in the urine. Relatively few metabolism studies have been done, but it is known that some ring hydroxylation (primarily in the para position) of the compound occurs in the liver. Novelli first showed that PBN could be used to protect experimental animals from septic shock (Novelli et al. 1986), and indeed this was later confirmed by other groups (Pogrebniak et al. 1992). The use of PBN and derivations as pharmacological agents began after discoveries in 1988 that showed that PBN had neuroprotective activity in experimental brain stroke models (Floyd 1990; Floyd et al. 1996; and Carney et al. 1991). These results were repeated and extended, (i.e. see References Clough et al. 1991; Cao et al. 1994; Folbergrovaet al. 1995; Pahlmark et al. 1996, for example). The present inventors have summarized the extensive neuroprotective pharmacological research effort on PBN and derivatives (Floyd 1997; Hensley et al. 1996). In addition to neurodegenerative diseases, PBN has been shown to protect in other pathological conditions where ROS-mediated processes are involved, including diabetes and many other conditions. The mechanistic basis of why PBN and some of its derivatives are so neuroprotective in experimental stroke and several other neurodegenerative models has not been completely elucidated yet. However, it is clear that its action cannot simply be explained by its ability to trap free radicals. In fact the present inventors' research effort on the mechanistic basis of PBN's action now shows that it is acting by suppressing gene induction (Floyd 1997; Hensley et al. 1996; Miyajima et al. 1995; Tabatabaie et al. 1996; and Hensley et al. 1997), most likely by acting on oxidation-sensitive signal transduction processes (Robinson et al. 1999). In fact PBN seems to be acting by suppressing signal transduction enhanced ROS formation by mitochondria (Hensley et al. 1998). These findings and ideas have arisen from the study of neurodegenerative processes. It should be emphasized, however, that PBNs action in preventing CD carcinogenesis may be different than those found in the neurodegenerative disease models. A specific mechanism of action does not limit the present invention.

PBN is Protective in Choline-deficiency Model

Earlier studies showed that PBN administered in drinking water was very protective in the CD-model. The results were assessed after 12 weeks on the regime (Nakae et al. 1998). The research brought out several important points (1) PBN, even at the lowest level, drastically reduced the size of neoplastic nodules (from 1.92 mm$^3$ in CDAA only to 0.33, 0.17 and 0.10 mm$^3$ for the CDAA plus PBN treated at 6, 30 and 60 mg/kg-day respectively, see Table 1 of Nakae et al. 1998).

There was less effect of PBN on nodule number, i.e. 190 per mm$^3$ for CDAA only to 170, 149 and 142 for the 6, 30 and 60 mg/kg- day respectively, (see Table 1 of Nakae et al. 1998). (2) PBN significantly reduced connective tissue proliferation. (3) Increasing concentrations of PBN reduced 8-OHdG content (a marker of DNA oxidation) in the CD-livers. (4) PBN reduced the amount of PGE$_2$ in the CD-livers by about 50% at the highest dose but it had no effect on COX-II expression, either the mRNA or protein level. In summary then the fact that the very lowest level of PBN decreased the nodule size by 83% but only decreased the nodule number by 11% indicates to us that nodule size is the most sensitive parameter to PBN treatment. There was some effect on PGE$_2$ levels but only at the highest levels of PBN and this probably had to do with it acting as a catalytic inhibitor of the enzyme per se.

To highlight the potency of PBN relative to other chemicals that have been tested in the CDAA model, it is instructive to compare results, which were obtained by the Nakae-Konishi group (see Mizumoto et al. 1994; Endoh et al 1996; and Nakae 1999). The data clearly show that PBN is the most effective compound tested in the CDAA regimen in reducing the size of the preneoplastic nodules and in preventing an increase in the 8-OHdG content. The effectiveness of PBN on nodule size is much more potent than comparable amounts of the other inhibitors, most of which are free radical scavengers. The only other compounds that seemed to have some effect, albeit at higher levels, were nordihydroguaiaric acid (NGDA) and CV3611. CV3611 is the fatty acid ester of ascorbate. NGDA at the 0.1% level lowered nodule size, by 39% and CV3611 at the 0.05% level caused a 44% lowering. In contrast, PBN at the lowest level amount given (6 mg/kg) decreased nodule size by 83%; and by 95% at the highest level. NGDA was tested because of its known inhibition of lipoxygenase activity, but it has also been recently shown to antagonize tyrosine kinases (Hensley 1998). BPB (p-bromophenocybromide) was used as an inhibitor of phospholipase A$_2$ activity but as the data show, this compound had little activity in suppressing the size of the nodules (Endoh 1996). Acetylsalicylic acid had some effect (but not nearly as potent as PBN) on nodule size and nodule number, as well as 8-OHdG content (Endoh 1999). Alpha tocopherol and ascorbate as well as trolox were studied by they had very little effect on any of the parameters (Mizumoto et al. 1994). It should also be noted that none, if any, of the inhibitors have any effect on fatty liver development. The wide variability in effectiveness of various antioxidants in this model and their lack of effect on fatty liver development seems to be a consistent finding. A striking case in point involves antioxidant effectiveness of compounds inhibiting lipid peroxidation in rat liver mocrosomes versus their action in the CDAA model. Data collected by Janzen et al. 1994 demonstrate that Trolox and BHT show quite striking activity in ability to inhibit rat liver microsome peroxidation (IC$_{50}$ of 40$\mu$M and 6$\mu$M respectively) whereas PBN is about one thousand-fold less effective (IC$_{50}$ =5 mM). Yet PBN is very effective in the CDAA model (Nakae et al. 1998) but BHT and Trolox are not (Ghoshal et al. 1990; Mizumoto et al. 1994). This comparison amply illustrates the point that the action of inhibitors in the CDAA model cannot simply be explained by their antioxidant or radical scavenging properties alone.

While earlier studies have indicated a possible connection between the occurrence of preneoplastic nodular lesions and the presence or absence of PBN in rats on a CDAA diet, those of skill in the art understand that these preneoplastic nodular lesions are not dependently predictable of frank cancer development. The present invention establishes that nitrone reductants such as PBN as its derivatives are in fact effective in inhibiting the development of actual cancerous lesions. Those of skill in the art will understand that this discovery has great implications for one of the major health problems of our day.

SUMMARY OF THE INVENTION

The present invention involves a method for inhibiting initiation or development of cancer or tumor development. The method comprises enterally administering an effective dose of a nitrone free radical trapping agent. The administering is preferably enteral by supplementing food or drink.

Any phenyl, alkyl-substituted nitrone is preferred in the practice of the present invention. This is a narrow definition because the basic core structure of the phenyl nitrone is so simple that there are only a few thousand practically synthesized derivatives. A preferred nitrone is an aryl N-alkyl nitrone. The alkyl is tertiary (tert) butyl although other alkyls, cycloalkyls and the like may be used. Preferred aryls are phenyl, 3-hydroxyphenyl and 4-hydroxyphenyl and the like. Both new aryls and alkyls may be used once one of skill in the art performs tests as described herein to identify effective nitrones, find optimal doses, delivery and timing schedules. Dietarily administering an effective dose of a nitrone free radical trapping agent to a subject is a preferred administrative route although other routes may be found effective in particular situations.

The present invention more preferably involves a method comprising enterally administering an effective dose of 3-hydroxyphenyl N-tert-butylnitrone or 4-hydroxyphenyl N-tert-butylnitrone to prevent or inhibit cancer. In most cases an effective dose is from about 0.5 to about 60 mg/kg body wt. per day. In one preferred embodiment, the present invention involves a method for inhibiting hepatocarcinogenesis, the method comprising dietarily administering to a subject an effective dose of at least one of phenyl N-tert-butylnitrone, 3-hydroxyphenyl N-tert-butylnitone or 4-hydroxyphenyl N-tert-butylnitrone. Subjects to be treated include those with a family history of cancer such as prostate, breast, liver or other cancer, as well as subjects believed to have been exposed to a carcinogenic environment such as excess UV irradiation, radiation, food contaminated with carcinogens, etc. In cases where the dietary administration is through supplementation of a food component, the nitrone content effective amount may be from about 0.005 w/w % to about 0.1 w/w % of the diet being administered.

Other tumor models where PBN and its chemical derivatives are likely to be active include HCC development caused by infection from hepatitis B virus and hepatitis C virus. Many tumors that afflict humans progress through a preneoplastic nodular stage and evidence indicates that ROS or conditions that exacerbate ROS formation are important in tumor development. Therefore, we consider it likely that the development of many human tumors may be held in check by daily administering of PBN or one of its effective chemical derivatives at very low levels (perhaps at 1 mg or less per day).

The present invention also involves a nitrone free radical trapping agent for use in the preparation of an anti-carcinogenic diet and the preparation of such supplemented diets. Again an aryl N-alkyl nitrone free radical trapping agent is preferred for use in the preparation of an anti-carcinogenic diet. The most preferred nitrones are 3-hydroxyphenyl N-tert-butylnitone and 4-hydroxyphenyl N-tert-butylnitrone, individually or in combination for use in the preparation of an anti-carcinogenic diet.

While earlier studies have indicated a possible connection between the occurrence of preneoplastic nodular lesions and the presence or absence of PBN in rats on a CDAA diet, those of skill in the art understand that these preneoplastic nodular lesions are not dependently predictable of frank cancer development. The present invention establishes that nitrone reductants such as PBN as its derivatives are in fact effective in inhibiting the development of actual cancerous lesions. Those of skill in the art will understand that this discovery has great implications for one of the major health problems of our day.

Examples where PBN (or its potent derivatives) are expected to be active in preventing frank tumor development included in addition to those in the liver, those that develop in most organs including stomach, colon, breast, pancreas, prostate, skin, head and neck, as well as the blood stream.

The present invention also involves a nitrone free radical trapping agent for use in the preparation of an anti-carcinogenic diet and the preparation of such supplemented diets. Again an aryl N-alkyl nitrone free radical trapping agent is preferred for use in the preparation of an anti-carcinogenic diet. More preferred nitrones are 3-hydroxyphenyl N-tert-butylnitone, 2-hydroxyphenyl N-tert-butylnitone, 2-sulfoxyphenyl N-tert-butylnitone and 4-hydroxyphenyl N-tert-butylnitrone, individually or in combination for use in the preparation of an anti-carcinogenic diet. Those subjects most likely to beneficially receive the nitrones of the present invention would include; 1) those having had pretumor tests indicating a high probability of the presence of tumors, 2) those exposed to very potent carcinogenic environments and their probability of tumor progression is high, and 3)to those whose genetic predisposition makes their likelyhood of tumor development high in the tumors that the particular nitrone will be effective in controlling

BRIEF DESCRIPTION OF THE DRAWINGS

FIG. 1 is a table showing the effects of PBN on the induction of HCA, HCC and fibrosis in rats fed the CDAA diet for 70 weeks.

FIG. 2 is a table showing the results of CDAA± various amounts of nitrones.

FIG. 3 is a table showing the results of the numbers and sizes of GST-P-positive liver lesions and levels of oxidative hepatocyte injuries of rats.

FIG. 4 is a table showing the results of apoptotic indices and grade of fibrosis in the livers of rats.

DETAILED DESCRIPTION OF THE INVENTION

The present invention relates to inhibitors of PBN and its derivatives on the development of hepatocellular carcinoma (HCC), for example, in animals fed a CDAA diet. The present invention also relates to a showing that PBN and its derivatives effectively inhibit the development of HCC induced by a chronic feeding of the CDAA diet. This chemopreventive action of PBN and its derivatives is suggested to result from both the disturbance of the development of preneoplastic lesions including HCA in the early phase and the prevention of their progression to HCC in the late phase of the dietary hepatocarcinogenesis.

Data recently collected from a long-term (70-week) study of the effectiveness of PBN (when in drinking water) in the CD-model, demonstrated that it completely inhibited frank HCC formation and was not carcinogenic itself. PBN is the most effective anti-carcinogenic compound tested thus far in this specific model. In follow-up studies, the inventors found that 4-hydroxy PBN (4-OH-PBN) when administered in the diet was even a more effective anti-carcinogen than the parent compound. Accordingly, PBN, as well as 4-OH-PBN 3-OHPBN,2-OHPBN and 2-SPBN (2 sulfoxy PBN), inhibit CD-mediated hepatocellular carcinoma development in rats when administered in the diet.

The abbreviations used herein are as follows: PBN, phenyl N-tert-butyl nitrone; iNOS, inducible nitric oxide synthase; NF-κB, nuclear factor-κB; COX2, inducible cyclo-oxygenase; CDAA diet, choline-deficient, L-amino acid-defined diet; GST-P, glutathione S-transferase placental form; HCC, hepatocellular carcinoma; HCA, hepatocellular adenoma; CSAA diet, choline-supplemented, L-amino acid-defined diet; iNOS, inducible nitric oxide synthase; COX, cyclo-oxygenase.

The following examples further illustrate model embodiments of the present invention including preferred versions and methods of making the same; however these examples are not to be construed as limitations of this invention.

EXAMPLE 1

The present example shows effects of phenyl N-tert-butyl nitrone (PBN), a radical trapping agent, on hepatocarcinogenesis in male Wistar rats fed a choline-deficient, L-amino acid-defined (CDAA) diet for 70 weeks. Hepatocelluar adenoma (HCA) and carcinoma (HCC) were induced with 57.1% incidences by continuous feeding of the CDAA diet for 70 weeks. PBN, administered in the drinking water at a concentration of 0.065% throughout the experimental period with the CDAA diet, reduced HCA and HCC incidences, both to 25.0%. When PBN for the first 26 weeks and then vehicle drinking water for 44 weeks were administered with the CDAA diet, both HCA and HCC incidences were reduced to 28.6 and 0%, respectively. In contrast, when vehicle drinking water for 26 weeks and then PBN for the last 44 weeks were administered with the CDAA diet, HCC incidence was reduced to 0%, but HCA incidence remained high as 62.5%. These results indicate that PBN inhibited hepatocarcinogenesis in rats fed the CDAA diet. The inhibition by PBN of the conversion from HCA to HCC in the late phase is especially important in the prevention of the HCC development.

PBN is a nitrone-based radical trapping agent possessing potent anti-oxidative activity (Kotake 1999). In addition, PBN has been shown to exert anti-nitrosative effects by inhibiting the induction of iNOS and to prevent alterations on the status of various signaling molecules like NF-κB, pro-inflammatory cytokines, COX2 and pro-apoptotic gene products in in vitro and/or in vivo occasions (Kotake 1999). Reflecting these properties, PBN is preventive against a variety of animal disorders such as endotoxin shock, ischemia-reperfusion injuries, nerodegenerative diseases and diabetes that are mediated by oxidative and nitrosative stresses and altered signal transduction (Kotake 1999).

Chronic feeding of the CDAA diet induces a high incidence of HCC within a year (in the absence of any known carcinogen) due to the endogenous mechanisms (Nakae et al. 1992; Nakae 1999; Nakae 2000). In this model, HCC is induced through GST-P-positive, foci of cellular alteration and then HCA under the background presence of continuous death and proliferation of hepatocytes and fibrosis resulting in cirrhosis (Nakae 1999).

In a previous report, the present inventors demonstrated that PBN inhibits the induction and growth of GST-P-positive foci of cellular alteration in the livers of rats fed a CDAA diet due to the inhibition of oxidative injury on hepatocyte nuclear DNA and of COX2 activity at the catalytic level (Nakae et al. 1998). Extending these findings, the present study assesses effects of PBN on the entire hepatocarcinogenesis in rats fed the CDAA diet, using HCC as an endpoint marker.

Materials and Methods

Animals, diets and chemical. The protocols were approved prior to the experiments by the Animal Experimentation committee at Nara Medical University according to the Guidelines on Animal Experiments in accordance with Japanese Government Animal Protection and Management Law Number 105 and Japanese Government Notification on Feeding and Safekeeping of Animals Number 6. Male Wistar rats, 6 weeks old, were purchased from JapanSLC, Inc., Hamamatsu, Shizuoka, Japan. Rats were housed 5 each to a plastic cage with white flake bedding (Kansai Animal Corp., City of Kyoto, Kyoto, Japan) in an air-conditioned room (25±3° C. temperature, 55 ±8% relative humidity, 10–12/h ventilation and 12-h dark/light cycle). Rats were used for the experimentation after a 1-week acclimation on a basal diet (CE-1, Clea Japan, Meguro, Tokyo, Japan) and allowed free access to food and tap water throughout the acclimation and experimental periods. Body weight, food consumption and water intake were monitored weekly. The CDAA diet and a control CSAA diet were obtained from Dyets Inc., Bethlehem, PA. PBN was synthesized and purified to 99.997% purity according to the method of Janzen and Haire (Janzen et al. 1990) in our laboratories.

Pilot study. A pilot study was conducted to determined a time-point when the late phase starts in hepatocarcinogenesis in rats fed the CDAA diet. A group of 20 rats were fed the CDAA diet for 16 weeks, and 10 animals were sacrificed. The remaining 10 rats were then fed the CSAA diet for 54 weeks and sacrificed 70 weeks after the commencement by exsanguination under light ether anesthesia. The other group of 20 rats were fed the CDAA diet for 26 weeks, and 10 animals were sacrificed. The remaining 10 rats were then fed the CSAA diet for 44 weeks and sacrificed 70 weeks after the commencement. Upon the sacrifice, the livers were taken, and 4-μm-thick, 10%-neutrally-buffered-formalin-fixed (for 24 h), paraffin-embedded specimens were prepared and stained routinely by a H&E procedure. The liver specimens were histologically examined according to the criteria described in the literature (Maronpot et al. 1996).

Main study. A total of 60 rats were equally divided into 6 groups. Group 1 received the CDAA diet for 70 weeks. Group 2 received the CDAA diet with PBN at a concentration of 0.065% in the drinking water for 70 weeks. Group 3 received the CDAA diet with PBN for 26 weeks and then the CDAA diet alone for 44 weeks. Group 4 received the CDAA diet alone for 26 weeks and then the CDAA with PBN for 44 weeks. Groups 5 and 6 received the CSAA diet alone and with PBN, respectively, for 70 weeks. The PBN dose was decided based on the inventors' previous report (Nakae et al. 1998). The time-point of 26 weeks after the commencement, when treatments were changed in groups 3 and 4, was decided according to the results of the pilot study (see the Results and Discussion section below). All surviving rats were sacrificed 70 weeks after the commencement, and the livers were taken. Two serial 4-μm-thick, 10%-neutrally-buffered-folmalin-fixed 9 for 24 h), paraffin-embedded liver specimens were prepared and stained routine H&E and Masson's trichrome procedures. The H&E-stained liver specimens were histologically examined according to the aforementioned criteria (Maronpot et al. 1986), and the incidences of HCA and HCC were determined. Grade of fibrosis were evaluated by analyzing percent area occupied by collagen fiber in the Masson's trichrome-stained liver specimens using an IPAP image analyzing system (Sumika Technoservice, Corp., City of Osaka, Osaka, Japan).

Statistical analyses. Statistical analyses were carried out using an InStat software (GraphPad Software, Inc., San Diego, Cali.). Fisher's exact test was used to assess statistical significance of inter-group differences of the lesion incidences. Student-Newrnan-Keuls multiple comparison test was used to assess statistical significance of inter-group differences of means after one-way ANOVA to determine variations among group means, followed by Bartlett's test to determine homogeneity of variance.

In the pilot study, foci of cellular alteration were induced in the livers of all rats fed the CDAA diet for 16 weeks, and these lesions were persistent even after the following feeding of the CSAA diet for 54 weeks. No HCAs or HCCs were observed in any of these rats. Using male Fischer 344 rats, it was similarly shown that foci of cellular alteration, but not HCAs or HCCs are induced by feeding the CDAA diet for 24 weeks and then the CSAA diet for 28 weeks (Nakae et al. 1992). It is suggested that a period of 16–24 weeks is not enough to induce HCAs or HCCs but sufficient to induce foci of cellular alteration maintaining themselves persistent but not have a potency to be converted into advanced forms in the absence of the additional carcinogenic stimuli. In contrast, HCAs were induced in 2 out of 10 rats (20% incidence) after feeding the CDAA diet for 26 weeks. When the CDAA diet for 26 weeks and then the CSAA diet for 44 weeks were fed, HCAs were observed in 2 out of 10 rats (20% incidence). These results demonstrate that chronic feeding of the CDAA diet for at least 26 weeks induces HCAs, and that HCCs are later induced even in the absence of the additional carcinogenic stimuli. These results of the pilot study suggest that the late phase of rat hepatocarcinogenesis may start 26 weeks after the beginning of feeding of the CDAA diet.

The results of the main study are summarized in the table of FIG. 1. Three, 2, 3, and 2 rats died in groups 1, 2, 3 and 4, respectively. All rats survived in groups 5 and 6. There were no differences among groups in terms of food consumption or water intake. The final body and relative liver weights of group 5 were higher and lower than those of group 1, respectively. The administration of PBN did not affect the final body or relative liver weights in groups 2, 3, 4 and 6. In group 1, the livers were macroscopically yellowish-white and appeared cirrhotic in association with a few large tumors with turbid and dark color. Histologically, HCAs and HCCs were both observed in 4 out of 7 rats (57.1% incidence), while all rats bared fatty liver and cirrhosis, 13.32% of liver specimen being occupied by collagen fiber. In group 2, the livers were macrosocipcally brownish-purple and with relatively smooth surface. Histologically, HCAs and HCCs were both observed only in 2 out of 8 group 2 rats (25.0% incidence), these incidences being significantly less than the group 1 values. While fatty liver was still evident, fibrosis was drastically reduced, only 9.95% of liver specimen being occupied by fiber, which was significantly less than the group 1 value. In group 3, macroscopic and histological characteristics of the livers resembled those of group 2. HCAs and HCCs were observed in 2 (28.6% incidence) and 0 (0% incidence) out of 7 rats, respectively, and 8.71% of liver specimen was occupied by fiber. These incidences and the grade of fibrosis were all significantly less than the group 1 values. In group 4, the livers almost appeared macroscopically, similarly to those of group 1, but lacked large tumors. Histologically, HCAs were observed in 5 out of 8 rats (62.5% incidence) with fatty liver and cirrhosis, 12.86% of liver specimen being occupied by fiber. These were all in the same range as group 1. HCCs, however, were not histologically observed (0% incidence), the incidence being significantly less than the group 1 value. No remarkable macroscopic or histological changes were detected in the livers of groups 5 or 6, and the incidences of HCAs and HCCs (both 0%) and grade of fibrosis (1.61%) were all significantly less than the group 1 values. These results clearly show that PBN inhibits the induction of HCCs in the livers of rats fed the CDAA diet. Such an inhibitory effect of PBN is suggested to be due to both the prevention of the HCA development, because of the reduced HCA and no HCC development by PBN administered only in the first 26 weeks, and of the conversion of HCAs into HCCs, because of the no HCC development without altering HCA incidence.

The present inventors' previous report demonstrates that PBN inhibits the induction and, more prominently, growth of GST-P-positive foci of cellular alteration by a 12-week feeding of the CDAA diet, which is attributed to its inhibition of oxidative stress and COX2 activity (Nakae et al. 1998). While the roles of reactive oxygen species and COX2 have been well indicated in the early phase of hepatocarcinogenesis in rats fed the CDAA diet, various other factors have also been suggested to participate (Nakae 1999; and Nakae 2000). Reactive nitrogen species and transcription factors like NF-κB may be involved, because 1'-acetoxychavicol acetate and PBN, both inhibitors of iNOS induction and NF-κB activation (Kotake 1999; Ohata et al. 1998), inhibit the induction of GST-P-positive foci of cellular alteration (Nakae 1999; Nakae 2000; and Nakae 1998). While a variety of signaling alterations are induced in the livers of rats fed a semipurified choline-deficient diet (Zeisel). The present inventors have shown the accumulation or altered status of NF-κB, caspase-1 and various cytokines also in the livers of rats during a 12-week feeding of the CDAA diet (Nakae 1999). Such alterations may also take part in the early phase of this hepatocarcinogenesis, because PBN can normalize these alterations (Kotake 1999). Signals relating to fibrosis may also participate, because reactive oxygen species and various signaling molecules are involved in the activation, proliferation and functioning of liver stellate cells inhibit the induction of both fibrosis and GST-P-positive foci of cellular alteration in the livers of rats fed the CDAA diet (Sakaida et al. 1996; Sakaida et al. 1998). Non-steroidal anti-inflammatory drugs, N-(4-hydroxyphenyl) retinamide and PBN inhibit the induction of fibrosis along with the inhibition of the induction and growth of GST-positive foci of cellular alteration (Nakae 1999; Nakae 2000; and Nakae et al. 1998). The present results suggest that the fibrotic processes are also involved in the induction of HCAs in the early phase and can be inhibited by PBN, but that the presence of cirrhosis itself may not affect the conversion of HCAs into HCCs in the late phase. Taken together, it is suggested that the inhibitory effects of PBN on the early phase of hepatocarcinogenesis in rats fed the CDAA diet result from its regulation of a wide range of signal transduction pathways.

Whereas little has been elucidated about the mechanisms underlying the late phase of hepatocarcinogenesis in rats fed the CDAA diet, hypomethylation of oncogenes has long been considered as one of the critical factors in rat hepatocarcinogenesis due to dietary deficiency in choline and multiple methyl group donors (lipotropes) (Poirier et al. 1994; and Christman 1995). The present inventors have recently shown that the 5'-flanking region of the c-myc gene is hypomethylated, resulting in overexpression of its mRNA in HCCs, but not HCAs, in rats fed the CDAA diet (Tsujiachi et al. 1995). It is conceivable that hypomethylation of the c-myc gene play roles in the acquisition of the malignancy by HCC converted from HCA. Reactive oxygen species lead epigenetic alteration in DNA methylation patterns under the intervention of transcription factors (Christman 1995; and Cerdra et al. 1997). PBN may disturb the formation of aberrant DNA methylation patterns by virtue of its inhibitory potency for oxidative stress and the activation of transcription factors (Kotake 1999), and in turn prevent the conversion of HCAs into HCCs. Furthermore, the transforming growth factor-β signaling pathway is altered in HCCs induced by the CDAA diet feeding (Sasaki et al. 2001). This may be another factor involved in the late phase mechanisms of hepatocarcinogenesis in rats fed the CDAA diet, and PBN may affect this process by its ability to normalize altered signal transduction (Kotake 1999).

In conclusion, PBN is chemopreventive against the induction of HCCs in the livers of rats fed the CDAA diet by inhibition of not only the HCA induction but also the conversion from HCAs to HCCs. Further studies are apparently demanded to evaluate chemopreventive effects of PBN against a wide variety of carcinogenic occasions and to elucidate the mechanisms underlying the cancer chemopreventive effects of PBN.

EXAMPLE 2

The present example extends previous results (Nakae, D., et al. (1998)) showing the anti-hepatocarcinogenic effects of a radical trapping agent, phenyl N-tert-butyl nitrone (PBN), by examining the effects of its derivatives on the early phase of hepatocarcinogenesis in rats fed a choline-deficient, L-amino acid-defined (CDAA) diet. Male Wistar rats, 6 weeks old, were fed the CDAA diet alone or containing PBN derivatives at concentrations of 0.009, 0.045 or 0.090% for 16 weeks. The number of glutathione S-transferase placental form (GST-P)-positive, putatively preneoplastic lesions, were decreased only by the highest dose of PBN. However, the size of the preneoplastic lesions as well as oxidative injury on hepatocyte extra-nuclear components were decreased by all doses of 4-hydroxy-PBN and the highest doses of PBN and 3-hydroxy-PBN. 4-hydroxy-PBN and 3-hydroxy-PBN enhanced cellular apoptosis in the GST-P-positive lesions, without inhibiting it in surrounding tissue. Only 4-hydroxy-PBN inhibited hepatocyte proliferation both in GST-P-positive lesions as well as in the surrounding tissue. Neither 2-hydroxy-PBN nor 2-sulfoxy-PBN exerted any of these effects. The present results demonstrate that PBN, 4-hydroxy-PBN and 3-hydroxy-PBN inhibit the growth of preneoplastic lesions. 4-hydroxy-PBN was more effective than PBN and 3-hydroxy-PBN. It is suggested that the metabolic conversion of PBN to 4-hydroxy-PBN plays an important role in the anti-hepatocarcinogenic effects of PBN, and that PBN, 4-hydroxy-PBN and 3-hydroxy-PBN may serve as useful cancer chemopreventive agents.

Chemoprevention by natural or synthetic chemicals has attracted attention in the potential control of cancers by delaying or arresting the carcinogenic (Chemoprevention Working Group 1999; and Hursting et al. 1999). Carcinogenesis is a multi-step process and therefore, it has been proposed that events occurring in each step can be targets for chemopreventive chemicals. Promising results have been obtained chiefly by investigations using appropriate in vivo animal models (Chemoprevention Working Group 1999; and Hursting et al. 1999).

Phenyl N-tert-butyl nitrone (PBN) is a nitrone-based free radical trapping agent that has been used in the detection of radical species by the spin-trapping technique. It has been shown to be potently effective in inhibiting in vitro and in vivo oxidative and nitrosative stress and signal transduction abnormalities (Kotake 1999). PBN administration to rats yields 4-hydroxy-PBN (4-OHPBN) as the single predominate metabolite (Reinke 2000). When PBN is administered to rats in vivo, free and conjugated forms of 4-OHPBN are detected in hepatic tissue, as well as in the bile, urine, and blood plasma (Reinke 2000). 4-OHPBN is, therefore, considered the major metabolite of PBN formed in the liver microsomal system and it is thought to play crucial roles in the pharmacological action of the parent compound (Kotake 1999, Reinke 2000). Little is known, however, about the biological effects of 4-OHPBN.

The present inventors have previously demonstrated that PBN inhibits the induction and, more prominently, the growth of glutathione S-transferase placental form (GST-P)-positive, putatively preneoplastic lesions, in the livers of rats fed a choline-deficient, L-amino acid-defined (CDAA) diet. PBN inhibits oxidative damage to hepatocyte nuclear DNA and suppresses inducible cyclo-oxygenase activity (Nakae et al 1998). The specific action of the anti-hepatocarcinogenic mechanism of PBN, however, still remain largely obscure. The present study was conducted to extend our earlier findings on the anti-hepatocarcinogenic effects of PBN, by examining the effect of 4-OHPBN, and other related derivatives on the early phase of rat hepatocarcinogenesis by chronic feeding of the PBN and derivatives in the CDAA diet.

Materials and Methods

Animals. A total of 110 male Wistar rats were obtained at 5 weeks of age from Charles River Japan, Inc., Atsugi, Kanagawa, Japan. Experimentation began after a 1-week acclimation on a basal diet (CE-2 diet, Clea Japan, Meguro, Tokyo, Japan). Rats were housed 5 each in plastic cages with white flake bedding (Kansai Animal Corp., City of Kyoto, Kyoto, Japan) in a standard atmosphere (temperature, 25±3° C.; relative humidity, 55±8%; ventilation, 10–15/hour; and a 12-hour dark/light cycle). Free access to food and tap water was allowed throughout the acclimation and experimental periods.

Diets and chemicals. The CDAA diet and its control, a choline-supplemented, L-amino acid-defined (CSAA) diet (Nakae et al. 1992; and Nakae et al. 1990) were obtained from Dyets, Inc., Bethlehem, Pa. PBN, 4-OHPBN, 3-hydroxy-PBN (3-OHPBN) and 2-hydroxy-PBN (2-OHPBN) were synthesized and purified to 99.997% purity in our laboratories (Janzen et al. 1990). 2-Sulfoxy-PBN (2-SPBN) was purchased from Aldrich Chemical Co. (Milwaukee, Wis.).

Animal experiment. After acclimation, rats were divided equally into 22 groups consisting of 5 animals each. Animals in group 1 received the CDAA diet alone. Groups 2, 3, and 4 received the CDAA diet containing PBN at concentrations of 0.009, 0.045, and 0.090% (hereafter referred as low, middle and high doses, respectively). Groups 5–7, 8–10, 11–13 and 14–16 received the CDAA diet containing the low, middle, and high doses of 4-OHPBN, 3-OHPBN, 2-OHPBN and 2-SPBN, respectively. Group 17 received the CSAA diet alone. Groups 18, 19, 20, 21, and 22 received the CSAA diet containing the high doses of PBN, 4-OHPBN, 3-OHPBN, 2-OHPBN, and 2-PBN, respectively. The doses of compounds were decided according to our previous report in which PBN was administered in the drinking water (Nakae et al. 1998). However in the present experiment we administered the compounds in the diet because of the limited solubility of the hydroxy-derivatives of PBN. All animals were sacrificed by exsanguination under light ether anesthesia 16 weeks after commencement, and the livers excised. Slices 5-mm-thick were taken from the left lateral, median and right lateral lobes of the livers, fixed in 10% neutrally-buffered formalin for 24 hours and then embedded in paraffin. Five serial 4-$\mu$m-thick sections were prepared from each fixed liver slice and used for histological and immunohistochemical assessment as described below. The remaining portions of the livers were immediately frozen under liquid nitrogen and stored at −80° C. until use.

Body weight and food and water intake were monitored weekly, and the average dosages of PBN and its derivatives were then calculated.

Histological and immunohistochemical assessments. Histological assessment was performed using sections routinely stained with hematoxylin/eosin and Masson's trichrome procedures. Gradation of fibrosis was quantitatively evaluated in groups 1, 4, 7, 10, 13, 16 and 17 by calculating the percent area occupied by collagen fiber stained blue by Masson's trichrome method using an IPAP image analyzing system (Sumika Technoservice Corp., City of Osaka, Osaka, Japan). GST-P-positive lesions were visualized immunohistochemically. Lesions consisting of more than 6 cells were quantified using the IPAP system as described elsewhere (Kishida et al. 2000). The amount of apoptosis and the cellular proliferative activity were determined in groups 1, 4, 7, 10, 13, 16 and 17, using the double staining techniques by combination of the GST-P immunohistochemistry as above with the in situ terminal deoxynucleotidyl transferase-mediated dUTP-biotin nick end-labeling method (Gold et al. 1994) and the enhanced polymer one-step staining method for proliferating cell nuclear antigen (Tsutsumi et al. 1995), respectively. Numbers of apoptotic and proliferating hepatocytes among the 1000–5000 hepatocytes in GST-P-positive lesions and 5000 hepatocytes in surrounding tissue were counted under light microscopy to obtain percentages that are hereafter referred as apoptotic and proliferative indices, respectively.

Determination of oxidative hepatocyte injuries. Levels of oxidative damage to the hepatocytes were determined on frozen liver samples. Oxidative damage to nuclear DNA was assessed as previously described, using the amount of 8-hydroxydeoxyguanosine (8-OHdG) to $10^6$ deoxyguanosine (dG) ratio as a parameter (Nakae et al. 1995). Oxidative injury to extra-nuclear components was assessed as described elsewhere, by determining picomole malondialdehyde equivalent (MDA eq.) levels of 2-thiobarbituric acid-reacting substances (TBARS) per milligram protein (Nakae et al. 1990).

Statistics. Inter-group differences in quantitative data for multiple groups were recognized to be significant, when p values smaller than 0.05 were obtained by the Dunnett multiple comparison test employed after one-way analysis of variance to determine the variation among the group means followed by the Bartlett's test to determine the homogeneity of variance. Inter-group differences in data for particular group pairs were considered significant, when p values smaller than 0.05 were obtained by Student's t-test or Welch's t-test in cases where the data showed Gaussian bell-shaped or non-Gaussian distributions, respectively.

Results

General findings. All rats survived throughout the experimental period. There were no differences among groups in terms of final body weights or average food intake (the table of FIG. 2). The relative liver weight of rats given the control diet, i.e. group 17 was lower than those on the CDAA diet (group 1); but neither PBN nor any of its derivatives caused significant alterations of the liver weight in animals receiving the control diet (the table of FIG. 2). The average dosage of PBN and its derivatives closely correlated with their doses of administration showing no differences among chemicals (the table of FIG. 2).

Effects of PBN and its derivatives on the numbers and sizes of GST-P-positive lesions. The numbers and sizes of the preneoplastic lesions are summarized in the table of FIG. 3. GST-P positive lesions were observed in groups 1–16. There were no lesions in group 17–22 and therefore they were significantly lower than that of group 1. PBN significantly decreased the number of the lesions only at the highest dosage to 52% of the group 1 value. PBN and its derivative at the two lowest levels show no affect on the number of lesions. In contrast, the sizes of the lesions were significantly decreased to 19 and 9% of the group 1 value by the high doses of PBN, 3-OHPBN and 4-OHPBN. 4-OHPBN exerted the greatest effect. The low, middle and high doses of 4-OHPBN reduced lesion sizes to 24, 19 and 18% of the group 1 value, respectively. The lowest dose of 4-OHPBN was as effective as its higher doses and also as effective as the highest dose of PBN and 3-OHPBN. Neither 2-OHPBN nor 2-SPBN had any affect on the number or sizes of the lesions.

Effects of PBN and its derivatives on the levels of oxidative hepatocyte injuries. 8-OHdG and TBARS data are also presented in the table of FIG. 3. The nuclear DNA content of 8-OHdG of group 17 was significantly lower than that of group 1. All doses of PBN, 4-OHPBN, and 3-OHPBN significantly inhibited the increased 8-OHdG content caused by the CDAA diet feeding. These effects lacked dose-dependency, and the magnitudes were not different among the three chemicals. Neither 2-OHPBN nor 2-SPBN decreased the 8-OHdG levels from those of group 1. None of the chemicals had any affect on the 8-OHdG content of animals on the control diet.

The TBARS level of group 17 was significantly lower than that of group 1. While only the high dose of PBN and 3-OHPBN significantly inhibited the enhanced level caused by CDAA feeding, all three doses of 4-OHPBN significantly exerted an effect. The low dose of 4-OHPBN was as effective as its higher doses and of the high doses of PBN and 3-OHPBN. Neither 2-OHPBN nor 2-SPBN affected the TBARS levels. None of the chemicals had any effect when given in the CSAA control diet.

Effects of PBN and its derivatives on hepatocyte apoptosis and proliferation in GST-P positive lesions and surrounding tissue. Apoptotic and proliferative indices in GST-P-positive lesions and the surrounding tissue are summarized in the table of FIG. 4. The apoptotic index in the surrounding tissue of group 17 was significantly less than that of group 1. The apoptotic indices were significantly lower in the lesions than in the surrounding tissue in group 1. The high doses of PBN, 4-OHPBN, and 3-OHPBN significantly increased the apoptotic indices in the lesions approximately 3–4 fold over the group 1 value, while significantly decreasing this index in the surrounding tissue to about 40%. As a result, the apoptotic indices became significantly higher in the lesions than in the surrounding tissue of these groups. The magnitude of the effect was not significantly different among the three chemicals. Neither 2-OHPBN nor 2-SPBN altered the apoptotic indices.

The proliferative index in the surrounding tissue of group 17 was significantly less than that of group 1. The proliferative indices were significantly higher in the lesions than in the surrounding tissue in group 1. Only the high dose 4-OHPBN significantly decreased the proliferative indices both in the lesions to approximately 31% of the group 1 value and in the surrounding tissue to about 49%. As a result, the proliferative indices in the lesions were still significantly higher than, but became close to, those in the surrounding tissue of group 17. None of the other chemicals had any effect on the proliferative indices in the control groups.

Effects of PBN and its derivatives on histological liver injury. In group 1, extensive fibrosis was histologically observed in association with fatty liver. None of the chemicals had any affect on fatty liver. PBN, 4-OHPBN and 3-OHPBN inhibited fibrosis, but neither 2-OHPBN nor 2-SPBN did not. The grades of fibrosis of groups 1, 4, 7, 10, 13, 16 and 17 are summarized in the table of FIG. 4. The group 17 value was significantly less than the group 1 value. The high doses of PBN, 4-OHPBN and 3-OHPBN were significantly lower in the grade of fibrosis from group 1 values. The magnitude of this effect did not differ among the three chemicals. The high dose of both 2-OHPBN or 2-SPBN had no affect on the grade of fibrosis. No particular histological changes were noted in groups 17–22.

Discussion

The present results demonstrate that PBN, 4-OHPBN and 3-OHPBN, but not 2-OHPBN or 2-SPBN, inhibit the early phase of hepatocarcinogenesis in rats fed the CDAA diet, and that 4-OHPBN exerts a greater effect than PBN and 3-OHPBN. Even though the number of GST-P-positive lesions were reduced to approximately half of the positive control level by the high dose of PBN, their sizes were decreased to around 20% or less by PBN, 4-OHPBN and 3-OHPBN. Because the numbers and sizes of enzyme-altered liver lesions have been considered to reflect the induction and growth of preneoplastic hepatocyte population (Pitot et al. 1989), it is thus suggested that 4-OHPBN and 3-OHPBN inhibit the growth of preneoplastic liver lesions more prominently than it does their induction. We have already noted this result for PBN (Nakae et al. 1998). Oxidative hepatocyte damage to both nuclear DNA and extra-nuclear components were inhibited by PBN, 4-OHPBN and 3-OHPBN, but not by 2-OHPBN or 2-SPBN. The inhibition profile for TBARS was identical to that for the sizes of GST-P-positive lesions. Because oxidative hepatocyte damage to nuclear DNA and extra-nuclear components are involved respectively in the induction and growth of preneoplastic hepatocyte population in rats fed the CDAA diet, (Nakae et al. 1994; and Kobayashi et al. 1998), it is conceivable that the inhibition of oxidative stress is an important clue for the anti-carcinogenic effects of PBN, 4-OHPBN and 3-OHPBN.

In the livers of rats fed the CDAA diet, hepatocyte apoptosis is induced and accumulates in close association with oxidative damage to hepatocyte extra-nuclear components from 3 days on (Yoshiji et al. 1992). This is the time when over production of hydrogen peroxide by hepatocyte mitochondria occurs (Hensley 2000). It is closely associated with the increase of TBARS levels (Yoshiji et al. 1992). The present results show that apoptosis is suppressed in GST-P-positive lesions when compared with the situation in surrounding tissue. It is suggested that, whereas oxidative stress influences signaling inducing apoptosis (Nose 2000) to eliminate altered hepatocytes (Lowe et al. 2000; and Wyllie et al. 1999), it appears that apoptotic signaling is dysregulated in some preneoplastic hepatocytes (Reed 1999) such that they acquire resistance to apoptosis allowing these cells capable of growing into preneoplastic lesions. The apoptotic signaling change in some preneoplastic cells is analogous to their acquirement of resistance to chemical toxicity during exogenous hepatocarcinogenesis (Farber 1006). In this context, it is conceivable that PBN, 4-OHPBN and 3-OHPBN may exert different effects on oxidative stress-mediated apoptotic events in preneoplastic and non-preneoplastic hepatocytes, leading to enhanced elimination of the former and maintenance of the latter. The inhibition of apoptosis in the tissue surrounding GST-P-positive lesions may be due to the inhibitory effects of PBN on pro-apoptotic signaling factors, such as the over-expression of tumor necrosis factor-α, interleukin-1α and 1-β, interferon-γ, c-fos, caspase-3 and fas-A (Pogrebniak et al. 1991; Robinson 1999; Sang et al. 1999; and Stewart 1999). In contrast, it is unknown and under active investigation in our laboratories as to why apoptosis was enhanced in GST-P-positive lesions by PBN and its active derivatives. One of the possible target molecules is nuclear factor-κB, because its activation is inhibited by PBN (Kotake et al. 1998). Autonomous proliferation in (pre)neoplastic cells is a result of various modifications of the regulating system for cell proliferation. This system has been considered as one of the most important targets for chemoprevention (Krupp et al. 2000; and Mori et al. 1999). In the liver of rats fed the CDAA diet, c-myc and c-Ha-ras are over-expressed within 2 days (Tsujiuchi et al. 1995), and then hepatocyte proliferation is induced in close association with the increase of TBARS from the third day (Yoshiji et al. 1992). The hepatocyte proliferation activity is higher in GST-P-positive lesions than in the surrounding cells as we demonstrated. In the present study, only 4-OHPBN inhibited hepatocyte proliferation. The inhibition was more prominent in GST-P-positive lesions than in the surrounding cells. This is probably one of the major reasons why the chemopreventive efficacy of 4-OHPBN is greater than PBN or 3-OHPBN.

Very little is known about the biological effects of the hydroxy-derivatives of PBN. We demonstrated that, at least in the present model that 4-OHPBN, 3-OHPBN and 2-OHPBN was more effective than, equal to, or much less effective than PBN, respectively. Clearly, the position of the hydroxy-group is important in the effectiveness of these PBN derivatives. It is highly likely that metabolic conversion to 4-OHPBN may play a significant role in the anti-hepatocarcinogenic effect of PBN. In contrast, the lack of the chemopreventive effects of 2-SPBN may be due to its hydrophilic property (Kotake 1999). The efficacy of the free radical trapping of 2-SPBN is as potent as, or in an aqueous environment, even stronger than PBN (Kotake 1999). Furthermore, 2-SPBN shows inhibitory effects on various disorders mediated by oxidative stress induced in the hydrophilic layer (Fallon et al. 1997; Harkins et al. 1997; and Schulz et al. 1995). N,N'-diphenyl-p-phenylenediamine, a lipophilic antioxidant, reduces the sizes of GST-P-positive lesions without affecting their numbers in the livers of rats fed the CDAA diet (Nakae et al. 1994). In this manner, it is similar to 4-OHPBN and 3-OHPBN. A lipophilic vitamin C derivative, 2-O-octadecylascorbic acid, inhibits rat hepatocarcinogenesis by chronic feeding in the CDAA diet greater than its hydrophilic parent, L-ascorbic acid (Mizumoto et al. 1994). The present results suggest that oxidative stress induced in the lipophilic layer is both an important mechanistic factor as well as a chemopreventive target in hepatocarcinogenesis in rats fed the CDAA diet.

In conclusion, PBN, 4-OHPBN, 2-OHBPN, 2-SOBPN and 3-OHPBN serve as useful cancer chemopreventive agents possibly by inducing apoptosis selectively in preneoplastic cells and inhibiting oxidative stress. Additionally, 4-OHPBN, a major metabolite of PBN, may be especially effective due to its additional ability to inhibit proliferation of preneoplastic cells.

References

The following citations are incorporated by reference herein for details supplementing this application:

Cao et al., "α-Phenyl-tert-butyl-nitrone Reduces Cortical Infarct and Edema in Rats Subjected to Focal Ischemia," *Brain Res.*, 644:267–272, 1994.

Carney et al., "Reversal of Age-related Increase in Brain protein Oxidation, Decrease in Enzyme Activity, and Loss in Temporal and Spacial Memory by Chronic Administration of the Spin-trapping Compound N-tert-butyl-α-phenyl-nitrone," *Proc. Natl. Acad. Sci. USA*, 88:3633–3636, 1991.

Cerda et al., "Influence of oxygen Ratical Injury on DNA Methylation," *Mutat. Res.*, 386:141–152, 1997.

Chemoprevention Working Group. (1999) *Cancer Res.* 59, 4743–4358.

Christman J. K., "Lipotrope Deficiency and Persistent Changes In DNA Methylation: Lipotrope Deficiency and DNA Methylation," *Adv. Exp. Med. Biol.*, 375:97–106, 1995.

Clough-Helfinan et al., "The Free Radical Trapping Agent N-tert-butyl α-phenylnitrone (PBN) Attenuates Cerebral Ischaemic Injury in Gerbils," *Free Radic. Res. Commun.*, 15:177–186, 1991.

Endoh et al., "Inhibition by Acetylsalicylic Acid, a Cyclo—Oxygenase Inhibitor, and p-bromophnacylbromide, a Phosphoipase $A_2$ Inhibitor, of Both Cirrhosis and Enzyme-Altered Nodules Caused by a Choline-Deficient, L-amino Acid-Defined Diet in Rats, "*Carcinogenesis*", 17:467–475, 1996.

Fallon, J., Matthews, R. T., Hyman, B. T. & Beal, M. F. (1997) Exp. Neurol. 144, 193–198.

Farber, E. (1996) *Adv. Cancer Res.* 70, 21–48.

Floyd et al., "Spin Trapping in biological Systems. Oxidation of the Spin Trap-5,5-dimethyl-1-pyrroline-1-oxide by a Hydroperoxide-hematin System," *Biochem. Biophys. Res. Comnmun.*, 74:79–84, 1977.

Floyd et al., "Role of Oxygen Free Radicals in Carcinogenesis and Brain Ischemia," *FASEB J.*, 4:2587–2597,1990.

Floyd et al., "Nitrone Radical Traps Protect in Experimental Neurodegenerative Diseases," In: *Neuroprotective Approaches to the Treatment of Parkinson's Disease and other Neurodegenerative Disorders*, edited by C. A. Chapman, C. W. Olanow, P. Jenner, and M. Youssim, London: Academic Press Limited, 1996, p. 69–90.

Floyd, R. A., "Protective Action of Nitrone-Based Free Radical Traps Against Oxidative Damage to the Central Nervous System," *Adv. Pharmacol.*, 38:361–378, 1997.

Floyd et al., "Inhibition by Phenyl N-tert-butyl Nitrone of Early Phase Carcinogenesis in the Livers of Rats Fed a Choline-Deficient, L-amino Acid-defined Diet," *Cancer Res.*, 58:4548–4551, 1998.

Folbergrova et al., N-tert-butyl-a-phenylnitrone Improves Recovery of Brain Energy State in Rats following Transient Focal Ischemia," *Proc. Natl. Acad. Sci. USA*, 92:5057–5061, 1995.

Gold, R., Schmied, M., Giegerich, G., Breitschopf, H., Hartung, H. P., Toyaka, K. V. & Lassmann, H. (1994) *Lab. Invest.* 71, 219–225.

Goshal et al., "Prevention by Free Radial Scavenger $AD_5$ of Prooxidant Effects of Choline Deficiency," *Free Radic. Biol. Med.*, 8:3–7, 1990.

Harkins, J. D., Carney, J. M., Meier, M., Leak, S. C. & Tobin, T. (1997) *Vet. Hum. Toxicol.* 39,268–271.

Hautekeete et al., "The Hepatic Stellate (Ito) Cell: Its role in Human Liver Disease," *Virchows Arch.*, 430:195–207, 1997.

Hensley et al., "Nitrone-based Free Radical Traps as Neuroprotective Agents in Cerebral Ischemia and Other Pathologies," In: *Neuroprotective Agents and Cerebral Ischaemia*, edited by A. R. Green and A. J. Cross, London: Academic press Ltd., 1996, p. 299–317.

Hensley et al., "Quantitation of Protein-bound 3-nitrotyrosine and 3,4-dihydroxyphenylalanine by High Performance Liquid Chromatography with Electrochemical Array Detection," *Anal. Biochem.*, 251:187–195, 1997.

Hensley et al., "Interaction of α-phenyl-N-tert-butyl Nitrone and Alternative Electron Acceptors With Complex I Indicates a Substrate Reduction Site Upstream from the Rotenone Binding Site," *J. Neurochem*, 71:2549–2557, 1998.

Hensley, K., Personal Communication, 1998.

Hensley, K., Kotake, Y., Sang, H., Pye, Q. N., Kolker, W. G. L., Tabatabaie, T., Stewart, C. A., Konishi, Y., Nakae, D. & Floyd, R. A. (2000) *Carcinogenesis* 21, 983–989.

Hursting, S. D., Slaga, T. J., Fischer, S. M., DiGiovanni, J. D. & Phang, J. M. (1999) *J. Natl. Cancer Inst.* 91,215–225.

Janzen, E.G., "Spin Trapping," *Acc. Chem. Res.*, 4:31–40, 1971.

Janzen, E. G. & Haire, D. L. (1990) in *Advances in Free Radical Chemistry*, ed. Tanner D. D. (JAI Press, Greenwich), pp. 253–295.

Janzen et al., "Comparison of Antioxidant Activity of PBN with Hindered Phenols in Initiated Rat Liver Microsomal Lipid Peroxidation," In: *Frontiers of Reactive Oxygen Species in Biology and Medicine*, edited by K. Asada and T. Toshikawa, Elsevier Science, 1994, p. 431–446.

Kishida, H., Nakae, D., Kobayashi, Y., Kusuoka, O., Kitayama, W., Denda, A., Kobayashi, Y., Nakae, D., Akai, H., Kishida, H., Okajima, E., Kitayama, W., Denda, A., Tsujiuchi, T., Murakami, A., Koshimizu, K., Ohigashi, H. & Konishi, Y. (1998) *Carcinogenesis* 19, 1809–1814. Fukui, H. & Konishi, Y. (2000) *Exp. Toxicol. Pathol.* 52,405–412.

Kotake, Y. (1999) *Antiox. Redox Signal.* 1, 481–499.

Kotake, Y., Sang, H., Miyajima, T. & Wallis, G. L. (1998) *Biochim. Biophys. Acta* 1448,77–84.

Krupp, G., Klapper, W. & Parwaresch, R. (2000) *Cell Mol. Life Sci.* 57, 464–486.

Lowe, S. W. & Lin, A. W. (2000) *Carcinogenesis* 21, 485–495.

Maronpot et al., "National Toxicology Program Nomenclature for Hepatoproliferative Lesions for Rats," *Toxicol. Pathol.*, 14:263–273, 1986.

Miyajima et al., "Spin Trapping Agent, phenyl-N-tert-butyl Nitrone, Inhibits Induction of Nitric Oxide Synthase in Endotoxin-induced Shock in Mice," *Biochem. Biophys. Res. Commun.*, 215:114–121, 1995.

Mizumoto, Y., Nakae, D., Yoshiji, H., Andoh, N., Horiguchi, K., Endoh, T., Kobayashi, E., Tsujiuchi, T., Shimoji, N., Denda, A., Tsujii, T., Nagao, M., Wakabayashi, K. & Konishi, Y. (1994) *Carcinogenesis* 15, 241–246.

Mori, H., Sugie, S., Yoshimi, N., Hara, Y. & Tanaka, T. (1999) *Mutat. Res.* 428, 291–298.

Nakae, D., Kotake, Y., Kishida, H., Hensley, K. L., Denda A., Kitayama, W., Tsujiuchi, T., Sang, H., Stewart, C. A., Tabatabaie, T., Floyd, R. A. & Konishi, Y. (1998) *Cancer Res.* 58, 4548–4551.

Nakae, D., Yoshiji, H., Mizumoto, Y., Horiguchi, K., Shiraiwa, K., Tamura, K., Denda, A. & Konishi, Y. (1992) *Cancer Res.* 52, 5042–5045.

Nakae, D., Yoshiji, H., Maruyama, H., Kinugasa, T., Denda, A. & Konishi, Y. (1990) *Jpn. J. Cancer Res.* 81, 1081–1084.

Nakae, D., Mizumoto, Y., Kobayashi, E., Noguchi, 0 & Konishi, Y. (1995) *Cancer Lett.* 97, 233–239.

Nakae, D., Yamamoto, K., Yoshiji, H., Kinugasa, T., Maruyama, H., Farber, J. L. & Konishi, Y. (1990) *Am. J Pathol.* 136, 787–795.

Nakae, D., Mizumoto, Y., Yoshiji, H., Andoh, N., Horiguchi, K., Shiraiwa, K., Kobayashi, E., Endoh, T., Shimoji, N., Tamura, K., Tsujiuchi, T., Denda, A. & Konishi, Y. (1994) *Jpn. J Cancer Res.* 85, 499–505.

Nakae D., "Endogenous Liver Carcinogenesis in the Rat," *Pathol. Int.*, 49:1028–1942, 1999.

Nakae D., "Modulation by Environmental Chemicals of Liver Carcinogenesis in Rats", *Recent Res. Devel. Cancer*, 2:143–165, 2000.

Nose, K. (2000) *Biol. Pharm. Bull.* 23, 897–903.

Novelli et al., "Anti-shock Action of Phenyl-tert-butylnitrone, a Spin Trapper," *In: Oxygen Free Radicals in Shock*, edited by G.P. Novelli and F. Ursini, Florence: Karger, Basel, 1986, page 119–124.

Ohata et al., "Inhibition by 1'-acetoxychavicol Acetate of Lipopolyvsaccharide- and Interferon-β-induced Nitric Oxide production Through Suppression of Inducible Nitric Oxide Synthase Gene Expression in RAW263 Cells," *Carcinogenesis*, (Lond.), 19:1007–1012, 1998.

Pahlmark et al., "Effects of the Spin Trap-α-phenyl-N-tert-butyl nitrone (PBN) in Transient Forebrain Ischaemia in the Rat," *Acta Physiol. Scand.*, 157:41–51, 1996.

Pitot, H. C., Campbell, H. A., Matonpot, R., Bawa, N., Rizvi, T. A., Xu, Y. H., Sargent, L., Dragan, Y. & Pyron, M. (1989) *Toxicol. Pathol.* 17, 594–612.

Pogrebniak, H., Matthews, W., Mitchell, J., Russo, A., Samuni, A. & Pass, H. (1991) *J. Surg. Res.* 50, 469–474.

Pogrebniak et al., "Spin Trap Salvage From Endotoxemia: The Role of Cytokine Down-Regulation," *Surgery*, 112:130–139, 1992.

Poirier L. A., "Methyl Group Deficiency in Hepatocarcinogenesis," *Drug Metab. Rev.*, 26: 185–199, 1994.

Poyer et al., "Spin Trapping of the Trichloromethyl Radical Produced During Enzymic NADPH Oxidation in the Presence of Carbon Tetrachloride or Carbon Bromotrichloromethane," *Biochim. Biophys. Acta*, 539:402–409, 1978.

Reed, J. C. (1999) *J. Clin. Oncol.* 17, 2941–2953.

Reinke, L. A., Moore, D. R., Sang, H., Janzen, E. G. & Kotake, Y. (2000) *Free Radic. Res. Biol. Med.* 28, 345–350.

Robinson, K. A., Stewart, C. A., Pye, Q. N., Nguyen, X., Kenney, L., Salzman, S., Floyd, R. A. & Hensley, K. (1999) *J. Neurosci. Res.* 55, 724–732.

Sakata et al., "the Prolyl 4-hydroxylase Inhibitor HOE077 Prevents Activation of Ito Cells, Reducing procollagen Gene Expression In Rat Liver Fibrosis Induced by Choline-Deficient L-amino Acid-defined Diet," *Hepatoloyy*, 23:755–763, 1996.

Sang, H., Wallis, G. L., Stewart, C. A. & Kotake, Y. (1999) *Arch. Biochem. Biophys.* 363, 341–348.

Sasaki et al., "Alterations of the Transforming Growth Factor-β Signaling Pathway in Hepatocellular Carcinomas Induced Endogenously and Exogenously in Rats," *Jpn. J. Cancer Res.*, 92:16–22, 2001.

Schulz, J. B., Henshaw, D. R., Siwek, D., Jenkins, B. G., Ferrante, R. J., Cipolloni, P. B., Kowall, N. W., Rosen, B. R. & Beal, M. F. (1995) *J. Neurochem.* 64, 2239–2247.

Stewart, C. A., Hyam, K., Wallis, G., Sang, H., Robinson, K. A., Floyd, R. A., Kotake, Y. & Hensley, K. (1999) *Arch. Biochem. Biophys.* 365, 71–74.

Tabatabaie et al., "In Vivo Trapping of Nitric Oxide in the Brain of Neonatal Rats Treated with the HIV-1 Envelope Protein gp 120: Protective Effects of α-Phenyl-tert-butylnitrone. *Biochem. Biophys. Res. Commun.*, 221:386–39-. 1996.

Tsutsumi, Y., Serizawa, A. & Kawai, K. (1995) *Pathol. Int.* 45, 108–115.

Tsujiuchi, T., Kobayashi, E., Nakae, D., Mizumoto, Y., Andoh, N., Kitada, H., Ohashi, K., Fukuda, T., Kido, A., Tsutsumi, M., Denda, A. & Konishi Y. (1995) *Jpn. J. Cancer Res.* 86,1136–1142.

Wyllie, A. H., Bellamy, C. O., Bubb, V. J., Clarke, A. R., Corbet, S., Curtis, L., Harrison, D. J., Hooper, M. L., Toft, N., Webb, S. & Bird, C. C. (1999) *Br. J. Cancer* 80, Suppl. 1, 34–37.

Yoshiji, H., Nakae, D., Mizumoto, Y., Horiguchi, K., Tamura, K., Denda, A., Tsujii, T. & Konishi, Y. (1992) *Carcinogenesis* 13, 1227–1233.

Zeisel S. H., "Nutrients, Signal Transduction and Carcinogenesis," *Adv. Exp. Med. Biol.*, 369:175–183, 1995.

What is claimed is:

1. A method for inhibiting the growth of a cancer comprising administering to a human subject with cancer a dose of a nitrone free radical trapping agent effective to inhibit the growth of said cancer.

2. A method for inhibiting tumor development comprising enterally administering to a human subject at risk of developing a tumor a dose of a nitrone free radical trapping agent effect to inhibit the development of said tumor.

3. A method for inhibiting a cancer comprising (a) identifying a human subject at risk of or having a cancer, and (b) dietarily administering to said human subject a dose of a nitrone free radical trapping agent effective to inhibit a cancer.

4. The method of claim 1, 2 or 3, wherein the agent is phenyl N-tert butylnitrone, 3-hydroxyphenyl N-tert-butylnitrone, 2-hydroxyphenyl N-tert-butylnitrone, 2-sulfoxyphenyl N-tert-butylnitrone or 4-hydroxyphenyl N-tert-butylnitrone.

5. The method of claim 1, 2, or 3, wherein the human subject has a familial history of cancer or has been exposed to a carcinogenic environment.

6. A method for inhibiting tumor development in a human subject comprising enterally administering an effective dose of 3-hydroxyphenyl N-tert-butylnitrone or 4-hydroxyphenyl N-tert-butylnitrone.

7. The method of claim 6, wherein the effective dose is from about 5 to about 60 mg/kg body wt. per day.

8. A method for inhibiting hepatocarcinogenesis comprising dietarily administering to a human subject a dose of at least one of phenyl N-tert-butylnitrone, 3-hydroxyphenyl N-tert-butylnitrone or 4-hydroxyphenyl N-tert-butylnitrone effective to inhibit hepatocarcinogenesis.

9. The method of claim 8, wherein the dietary administration is through supplementation of a food component.

10. The method of claim 8, wherein the human subject has been exposed to or infected with hepatitis B virus or hepatitis C virus.

11. The method of claim 8, wherein the effective amount is from about 0.005 w/w % to about 0.1 w/w % of the diet being administered.

12. The method of claim 1, 2, or 3 wherein the cancer is selected from the group consisting of liver, stomach, colon, breast, pancreas, prostate, skin, head and neck, and blood tumor cells.

13. The method of claim 1, 2 or 3, wherein the nitrone free radical trapping agent is an N-alkyl nitrone free radical trapping agent.

* * * * *